United States Patent [19]

Bennett

[11] Patent Number: Plant 6,454

[45] Date of Patent: Dec. 13, 1988

[54] MINIATURE ROSE PLANT 'SITTING PRETTY'

[76] Inventor: Cecilia L. D. Bennett, 489 Minot Ave., Chula Vista, Calif. 92010

[21] Appl. No.: 10,719

[22] Filed: Feb. 4, 1987

[51] Int. Cl.[4] ..... A01H 5/00

[52] U.S. Cl. ..... Plt./9

[58] Field of Search ..... Plt./9

*Primary Examiner*—James R. Feyrer

[57] ABSTRACT

The subject of the present disclosure is a new and distinct variety of miniature rose plant, named 'Sitting Pretty', which is characterized by its pale pink blooms, ranging from near Neyron Rose to near Empire Rose with a blending of near Chinese Coral to near Peach at the base of each petal, and a pale yellow reverse, ranging from near Empire Yellow to near Aureolin. The blooms are usually borne one to a stem with hybrid tea form. The bush is vigorous, well-branched and produces a moderate to heavy quantity of bloom.

1 Drawing Sheet

The present invention relates to a new and distinct variety of a hardy, dwarf, bush plant of the miniature class; the variety being primarily characterized as a pink blend.

The variety is further characterized by:

Long stemmed blooms of hybrid tea-type form, borne usually one to a stem but on occasion in sprays of 3 to 5 or more. The blooms are held very erect and well above the foliage.

It has a slight fragrance.

The plant ranges in height from 24 to 36 inches (approximately 60 to 90 cm). The canes are sturdy and erect with moderate branching and medium to heavy foliage covering. The plant is a moderate to heavy bloomer that does well either in the greenhouse or outdoors.

The plant has good growth habits, well-shaped and attractive, bearing numerous leaflets of average size.

The seed parent was Sonoma (U.S. Plant Pat. No. 3,302), and the pollen parent was Mabel Dot (miniature rose plant, orange-red; Dot; introduced by Minier, 1966). It differs from its seed parent in the following ways. It is a miniature rose of the pink blend color class, and Sonoma is a floribunda of the medium pink color class. It differs from its pollen parent in the following ways. It is a pink blend with hybrid tea form that is usually borne one to a stem, and Mabel Dot is an orange-red which has lower petal count and loose cupped blooms that are usually borne in compact clusters.

The descriptive matter which follows pertains to roses grown and color values observed in plants and newly opened blooms in the months of March through August 1986. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Sitting Pretty', the following is a detailed description thereof in outline; all major color plate identifications being by reference to the British Colour Council Horticultural Colour Chart, except where common terms of color definition are employed.

Type: Hardy, spreading, greenhouse or outdoor, decorative or exhibition potted plant.

Class: Miniature.

Variety name: Sitting Pretty.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Variable in length (30 to 40 mm); average diameter and sturdy; ranging in color from near Spinach Green (0960/30to 0960/2 page 0960) to near Lettuce Green (861/3 to 861/2 page 861) with some tinting of bronze.

*Hairs.*—Extremely small and numerous with a reddish color; located over the entire surface of the peduncle and sepals, but not present on the calyx tube.

*Calyx.*—Color ranging from near Spinach Green (0960/3 to 0960/2 page 0960) to near Lettuce Green (861/3 to 861/2 page 861).

*Opening.*—Opens well in all weather.

Bloom:

*Size when fully opened.*—Average for a minature variety (30 to 40 mm).

*Petalage.*—Double; averaging 35 to 40 petals, arranged regularly, plus petaloids (3 to 5 or more).

*Form.*—Urn-shaped to ovoid as the bloom progresses. The petals remain at first somewhat cupped with the apex and/or margins reflexed outward, becoming at maturity more loosely cupped; and the petals reflex more tightly (quilling), until each row of petals forms a five-pointed star.

Petals: Fairly thick with good substance; both the upper and under surfaces of all petals have a matte finish.

*Shape.*—Outer petals are of a very broad obovate form. The intermediate petals are very much like the outer petals only narrower. The inner petals are a broad lanceolate form; and the petaloids are also lanceolate form with some occasional irregularities.

Color: Newly opened flowers from plants grown outdoors (March through August 1986), Chula Vista, Calif.

*Outside petals.*—Upper surface—Outer half of petals range from near Neyron Rose (623/3 to 623/2 page 623) to near Empire Rose (0621/3 to 0621/2 page 0621) blending to lower half of petals which range from near Chinese Coral (614/2 to 614/1 page 614) to near Peach (512/1 to 512 page 512). Under surface — Outer margin ranges from near Neyron Rose (623/2 to 623/1 page 623) to near Empire Rose (0621/2 to 0621/1 page 0621) blending to the base of each petal which ranges from near Empire Yellow (603/1 to 603 page 603&) to Aureolin (3/2 to 3/1 page 3).

*Intermediate and inner petals.*—Upper surface — Outer half of petals range from near Neyron Rose (623/2 to 623/1 page 623) to near Empire Rose (0621/2 to 0621/1 page 0621) blending to lower half of petals which range from near Chinese Coral (614/2 to 614/1 page 614) to near Peach (512/1 to 512 page 512). Under surface — Ranging from near Empire Yellow (603/1 to 603 page 603) to near Aureolin (3/2 to 3 page 3).

*General color effect.*—Newly opened flowers — Pale pink with a base of yellow and a pale yellow reverse with a blending of pink at the upper margins. Three days open — Some fading of the color, especially the yellow tones. Five to seven days — Increased fading of yellow with touches of blush present on the margins of the petals. Quilling effect present on all petals. After seven days — Petals fading to near white with deep blush overlaying all sun-exposed surfaces.

*Flower longevity.*—(March through August 1986) Plant in pot 3 to 5 days from bud with sepals reflexed to fully opened bloom. Holding at fully opened with gradual fading of color for 3 to 5 days or longer. Cut blooms at living room temperature 4 to 7 days or longer.

Reproductive organs:

*Stamens.*—A generous amount arranged uniformly around the pistil.

*Filaments.*—Varying in length with shorter filaments more proximal to the pistil; golden yellow including the anthers.

*Pollen.*—Abundant.

*Pistil.*—Long, abundant and spreading; pale yellow at the base to reddish at the top with pale yellow caps on the styles.

*Ovaries.*—All encased in calyx.

*Hips.*—Some.

*Seeds.*—3 to 5 or more in each hip.

*Sepals.*—Permanent; spear-shaped with occasional small lanceolate foliage attached to the margins, giving the bud a somewhat 'lacey' or 'fringed' appearance; opens as the bloom opens, recurving against the peduncle, when the bloom is fully opened.

Foliage:

*Leaves.*—Five to seven leaflets on the average; medium size for a miniature rose plant.

*Leaflets.*—Broad ovate-shaped.

*Margin.*—Very serrated with tinting of bronze, especially noticeable on the newer foliage.

*Color.*—Ranging from near Spinach Green (0960/2 to 0960/1 page 0960) to near Lettuce Green (861/3 to 861 page 861) with occasional bronzing of the margins, especially noticeable on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 3 to 5 small thorns.

*Stipules.*—Varying in length from small to medium; average width; tapering auricles angled outward at about 45 degrees.

Growth:

*Habit.*—Upright and spreading; average to tall height for a miniature rose plant.

*Growth.*—Vigorous and well-branched.

*Canes.*—Medium diameter; sturdy; held erect.

*Main stems.*—Color — Ranging from near Spinach Green (0960/2 to 0960/1 page 0960) to near Lettuce Green (861/3 to 861 page 861) with occasional tinting of bronze, especially on the newer stems.

*Thorns.*—Averaging 15 to 20 per 10 cm on the main stems and fewer on the branches. Reddish in color; small to average in size; slender and straight.

*Branches.*—Color — Same as main stems.

The miniature rose plant and its flowers as herein described may vary in slight detail due to climate, soil and cultural conditions under which the variety may be grown; the present description being of the variety as grown at Chula Vista, Calif. I have found this variety to be easily asexually reproduced from cuttings.

The following is claimed:

1. A new and distinct variety of miniature rose plant, named 'Sitting Pretty' of hardy, dwarf, vigorous growth, well-branched and attractive in appearance, substantially as illustrated and described, characterized by its blooms of pale pink, ranging from near Neyron Rose to near Empire Rose, with a base, ranging from near Chinese Coral to near Peach, and a reverse of pale yellow, ranging from near Empire Yellow to near Aureolin.

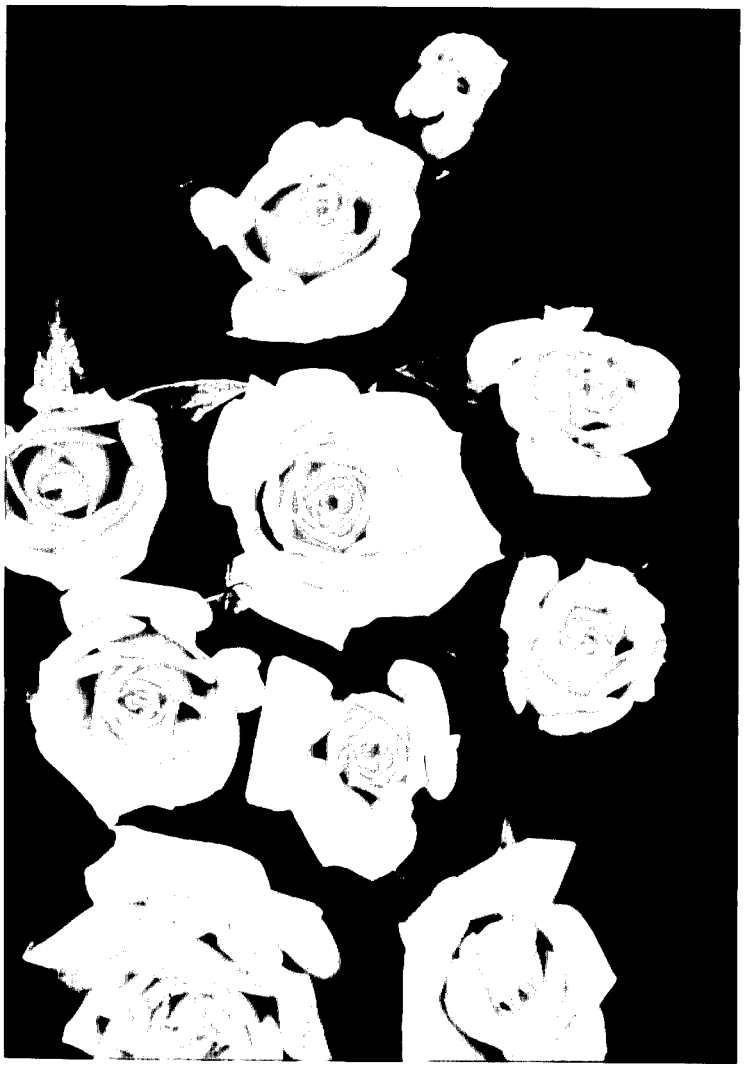

* * * * *